(12) United States Patent
Bishop

(10) Patent No.: US 9,297,795 B2
(45) Date of Patent: Mar. 29, 2016

(54) MONITORED FILAMENT INSERTION FOR RESITIVITY TESTING

(76) Inventor: Todd Nicholas Bishop, Bellingham, WA (US)

( * ) Notice: Subject to any disclaimer, the term of this patent is extended or adjusted under 35 U.S.C. 154(b) by 1326 days.

(21) Appl. No.: 12/959,370

(22) Filed: Dec. 3, 2010

(65) Prior Publication Data

US 2012/0139739 A1    Jun. 7, 2012

(51) Int. Cl.

| | |
|---|---|
| *G01N 33/44* | (2006.01) |
| *G01R 27/26* | (2006.01) |
| *B23B 51/00* | (2006.01) |
| *G01N 27/04* | (2006.01) |
| *B21J 5/06* | (2006.01) |
| *E21B 47/12* | (2012.01) |

(52) U.S. Cl.
CPC .............. *G01N 33/442* (2013.01); *B21J 5/066* (2013.01); *B23B 51/00* (2013.01); *E21B 47/12* (2013.01); *G01N 27/048* (2013.01); *G01R 27/2617* (2013.01); *G01N 2203/0053* (2013.01)

(58) Field of Classification Search
CPC .. B23K 20/122; B23K 20/123; B23K 20/125; G01R 1/06; G01R 15/16; G01R 27/16; G01R 27/2617; G01R 27/2676; G01R 27/2688; G01R 27/2694; G01R 31/025; G01N 27/048; G01N 33/442
USPC ................ 72/29.2, 30.1, 70.71, 342.1, 342.5; 228/2.1, 112.1; 438/17, 18; 324/354, 324/355, 356
See application file for complete search history.

(56) References Cited

U.S. PATENT DOCUMENTS

| | | | |
|---|---|---|---|
| 1,905,412 A * | 4/1933 | Kasson ..................... 324/552 |
| 2,364,957 A | 8/1939 | Norel | |
| 2,354,887 A | 10/1942 | Silverman et al. | |
| 2,382,639 A | 6/1944 | Kennard | |
| 2,536,333 A | 3/1948 | Waxelbaum | |
| 3,252,155 A | 5/1966 | Surtees et al. | |
| 3,550,481 A | 12/1970 | Jensen | |
| 3,939,683 A | 2/1976 | van Geffen | |
| 4,023,102 A * | 5/1977 | Barrow et al. ............... 324/537 |
| 4,110,739 A | 8/1978 | Kidd | |
| 4,432,037 A | 2/1984 | Brabetz | |
| 4,542,843 A * | 9/1985 | Middleton ................. 228/114.5 |
| 4,609,873 A * | 9/1986 | Cox et al. ................... 324/338 |
| 4,912,415 A * | 3/1990 | Sorensen ................... 324/347 |
| 5,214,387 A | 5/1993 | Fenner | |
| 5,469,062 A * | 11/1995 | Meyer, Jr. .................. 324/338 |
| 5,585,170 A * | 12/1996 | Morris et al. ............... 442/398 |
| 5,663,649 A * | 9/1997 | Topp et al. ................. 324/643 |
| 5,713,507 A * | 2/1998 | Holt et al. ................. 228/112.1 |
| 5,735,446 A * | 4/1998 | White et al. .............. 228/114.5 |
| 5,801,537 A * | 9/1998 | Siddiqui et al. ............ 324/643 |
| 5,829,664 A * | 11/1998 | Spinella et al. .......... 228/112.1 |
| 6,144,030 A * | 11/2000 | Ray et al. ................. 250/338.4 |
| 6,727,719 B2 * | 4/2004 | Liao et al. ................. 324/754.2 |
| 6,811,632 B2 * | 11/2004 | Nelson et al. ............. 156/73.5 |
| 6,866,181 B2 * | 3/2005 | Aota et al. ............... 228/112.1 |
| 6,873,162 B1 * | 3/2005 | Bois et al. ................. 324/638 |
| 7,049,967 B2 * | 5/2006 | Grasselli et al. .......... 340/573.1 |

(Continued)

*Primary Examiner* — Edward Tolan

(57) ABSTRACT

A friction-flow piercing apparatus for piercing very deep and fine holes is described, that relies on a novel support method for the piercing means. An apparatus for monitoring during the piercing process to determine the electrical properties gradient of the substrate is further described, particularly for meltable dielectric such as plastic industrial equipment. A permanently installed piercing means may function as a permanent test site.

20 Claims, 4 Drawing Sheets

(56) References Cited

U.S. PATENT DOCUMENTS

| | | |
|---|---|---|
| 7,121,448 B2 * | 10/2006 | Subramanian et al. ......... 228/2.1 |
| 7,156,277 B2 * | 1/2007 | Ishikawa et al. ............... 228/2.1 |
| 7,218,600 B2 * | 5/2007 | Cho et al. ...................... 369/126 |
| 7,696,021 B2 * | 4/2010 | Mehta et al. ................... 438/149 |
| 8,164,021 B1 * | 4/2012 | Ferrando ...................... 219/78.13 |
| 8,466,386 B2 * | 6/2013 | Wang et al. ................... 219/117.1 |
| 8,570,045 B2 * | 10/2013 | Tchakarov et al. ............ 324/369 |
| 8,878,093 B2 * | 11/2014 | Wang et al. ................... 219/117.1 |

* cited by examiner

MONITORED FILAMENT INSERTION FOR RESITIVITY TESTING

BACKGROUND OF THE INVENTION

1. Field of Invention

This invention relates generally to the field of piercing, using very fine filaments or piercing tools and to the support of the filaments during the friction-flow piercing process. The invention further cites a testing apparatus and method that relies on the cited piercing method for determining the moisture content of strata in a semi permeable dielectric solid 17.

2. Background of the Invention

The method described and reduced to practice herein, is uniquely useful and practical because it may be applied to fully assembled and cured parent material. It may be applied even while the equipment is in place and running. In addition, the electrical properties are recorded and may be compared with the depth of the filament in real time so that a conductivity profile of the solid thickness is created This invention is a novel means of supporting an extremely thin and long (high aspect ratio) piercing rod so that it does not buckle under the pressure of a friction-flow piercing operation. The cited piercing method is applied to a test apparatus for testing sub-surface saturation of dielectric solids that are being permeated by conductive fluids. One particular application would be testing of fiberglass (FRP) laminates in industrial chemical services.

The current invention relies on a friction piercing method using a rapidly rotating metallic filament to pierce through a meltable solid substrate 15. The tip of the piercing tool gets very hot from friction, liquefying the solid and causing it to flow along the filament creating a path for the advancement of the filament. No specific chip path is required with friction-flow piercing. The liquefied material flows out along the rotating piercing means. Once the rotation stops, the piercing means is either withdrawn or the liquefied material solidifies, sealing it in place. Since the filament is extremely thin and is inserted without pre-drilling, and if it is constructed from a metal that is chosen for excellent corrosion resistance, insertion will not degrade the substrate and filament can be used as a conductor to allow testing of substrates for electrical properties throughout the remainder of its life. Testing therefore, can be continuous during piercing and on-going after the installation.

Fiberglass (FRP) is notoriously difficult to test by common conventional means because it is highly irregular, full of anomalies, non-magnetic and normally non-conductive. The major testing companies do not attempt to test industrial FRP. There are ways, practiced by the inventor and other specialists in the field to get a reasonably accurate overall thickness measurement, but FRP saturates and often breaks down internally without losing overall thickness.

This testing method allows non-destructive detection of saturation within dielectric solids, and has many other known uses as well. The inventor believes that this method will make Industrial FRP safer and more reliable to use, and may contribute positively to other industries.

The method is simple and field practical and installation takes only few minutes using relatively inexpensive raw materials and installation equipment. Once inserted, the filament may be sealed in place making them extremely robust. The process is essentially non-destructive, and if the filament remains in the laminate and is sealed in place 20, with an end exposed for electrical contact 21, it becomes a permanent test site to detect changes in electrical resistance of the dielectric material 15 by measuring the impedance between the piercing means 1 and the conductive material 18 on the opposing surface 17. This assumes that the conductive material is either earth grounded or shares a direct electrical connection with the meter 11.

In the preferred embodiment, the filament is about 0.01" diameter, which is too small to cause significant structural interruption in most applications. It is important that the filament is as thin as possible, and that it is self-pierced into the surface, remaining in place to reduce the possibility of escapement of process fluids or gasses during or after the test.

It is understood that the piercing means may be made from but not limited to, tantalum, tungsten, steel, graphite, carbon, bonded carbides of alloys, or coated combinations thereof. Under some circumstances, it may be desirable to coat the length of the filament with a non-conductive coating so electrical measurements originate only from the piercing end of the filament. Coatings must be abrasive, heat and corrosion resistant and may include, but are not limited to ceramic or glass.

The invention teaches a unique means for supporting a very thin piercing member. By encapsulating the slender piercing rod in a low melt temperature plastic sheath such as styrene, a combination is produced that is stiff enough to pierce a hole with depth more than 300 times the diameter of the piercing means without relying on elaborate mechanical external support. The plastic simply melts away 19 from friction at the surface as the piercing tool enters the substrate 15. This method has proven extremely practical and is expected to be valuable to other applications as well.

PRIOR ART

The use of electrical properties testing including capacitance, resistance, and current flow to predict saturation of FRP has long been known, and there are expired and current patent cases on the record.

To our knowledge, conductive piercing tools have not been patented. Conductive fluted and abrasive drill bits have been patented for testing purposes in two applications;

a. Deep drilling into the earth for mineral exploration and extraction to identify deep earth layers and structures, and b. A single expired patent for a test method to detect the planar position of embedded conductive layers in printed circuit boards by probing with a conductive metal drill bit. It will be shown that neither application conflicts with the current invention.

Down-hole drilling for oil or minerals does not use a fluted drill, but is very different than flow piercing in that the bit turns slowly and abrades the rock and the debris is carried away by a steady stream of aqueous drilling fluid. Both fluted drill bits and abrasive drill bits such as down-hole drills rely on chip or debris relief paths to clear material, so they are inherently unsuitable for the purposes of this invention.

Friction-flow piercing refers to a process as defined by several expired patents wherein a high speed pointed, but not fluted steel piercing means, is pressed into a sheet metal surface while rotating at high speed. Friction melts the sheet metal, causing it to flow so that a hole is created in the sheet metal, with a build-up of metal around it to reinforce the hole and facilitate threading if desired. This type of operation requires high rotational speeds to achieve melt temperature for penetration. More speed is required with small diameter tools.

Existing patent applications teach collapsible drill support mechanisms of various types. One in particular describes a telescoping assembly comprised of multiple support locations. None mention the use of a meltable plastic sheath for this purpose.

Friction-Flow Piercing

U.S. Pat. No. 3,939,683 van Geffen et. al. Cites flow or friction piercing for metallic substrates. Representative of patents citing unsupported piercing friction tools that are primarily used to create bosses for threaded holes in sheet metal. Thin filaments and support means against buckling are not cited.

Drill Support

U.S. Pat. No. 2,362,639 Harry M. Kennard—Cites a telescoping tubular drill guide for extended, small diameter drills with exchangeable drill bushings. The invention utilizes two drill bushings per telescoping section so it provides multiple collapsing mechanical supports for a drill shaft. Given the length of the telescoping sections shown and required for necessary stability, this invention probably cannot collapse to a small enough thickness to be useful on a very fine filament. Also, threading a filament though this invention would be time consuming at each use.

U.S. Pat. No. 2,536,333 Sydney Waxelbaum—Cites a needle piercing machine for stacked fabrics that mechanically retracts a lower and mid bushing during the piercing process. This provides support at the extreme end and middle of the needle. This would not be sufficient for a filament with a diameter to length ratio of more than 100. This is a piercing operation, but not a friction piercing one. It rotates to help move fibers out of the way of the needle tip and reduce friction, but specifically avoids heat and burning of the sewing fabric.

U.S. Pat. No. 3,550,481 Harry M Jensen—Cites a retractable drill guide having an adjustable depth-stop.

Electrical Testing:

U.S. Pat. No. 4,110,739 John A Kidd Cites a method for detecting leaks in a composite tank by measuring the electrical conductivity between a conductive fiber layer in the laminate serving as a reference electrode buried behind a thermoplastic inner layer and conductive material inside a tank or vessel.

U.S. Pat. No. 3,252,155 Surtees et. al.—Cites a continuous monitoring system for a solid fiberglass tank having a conductive fiber layer behind the inner surface as the sub-surface reference electrode.

U.S. Pat. No. 5,214,387 Richard D Fenner—Cites electrical monitoring of multiple conductive sensors embedded in the dielectric solid. No means or method of installation is claimed. The system requires multiple embedded "sensors" at each site and a separate "channel" or conductor to allow external electrical access to the sensor. It would be impossible to install this invention while the equipment is running. The apparatus, applications, and results are distinct from the current invention.

Conductive Drilling Means:

U.S. Pat. No. 2,354,887 Daniel Silverman et. al. Is the earliest patent relying on a conductive drill string to monitor electrical properties of sub surface structures. It is specific to geological applications and does not rely on a conductive fluid on the opposite side, presumably because that would be too far to drill.

U.S. Pat. No. 2,364,957 Novel Douglas This application is typical of an early patent on the technique of "bore-hole logging". "Logging" is the process of identifying sub-surface structures in the earth during or after oil or mineral drilling. In this application, the drill is conductive at the tip and current flow or absorption (capacitance) is measured as the drilling proceeds. A continuous record of the electrical properties at depth is recorded and referred to as "Logging" the bore hole.

U.S. Pat. No. 4,432,037 Bernhard Brabetz Relies on a conductive drill bit to sense conductive layers in printed circuit boards. In particular, it is used in conjunction with a pre-designed test pattern in the board, allowing discovery of the relative position of all of the various layers before the board is completed. The test drill does not remain part of the circuit board.

PREFERRED EMBODIMENT

Figure 1:
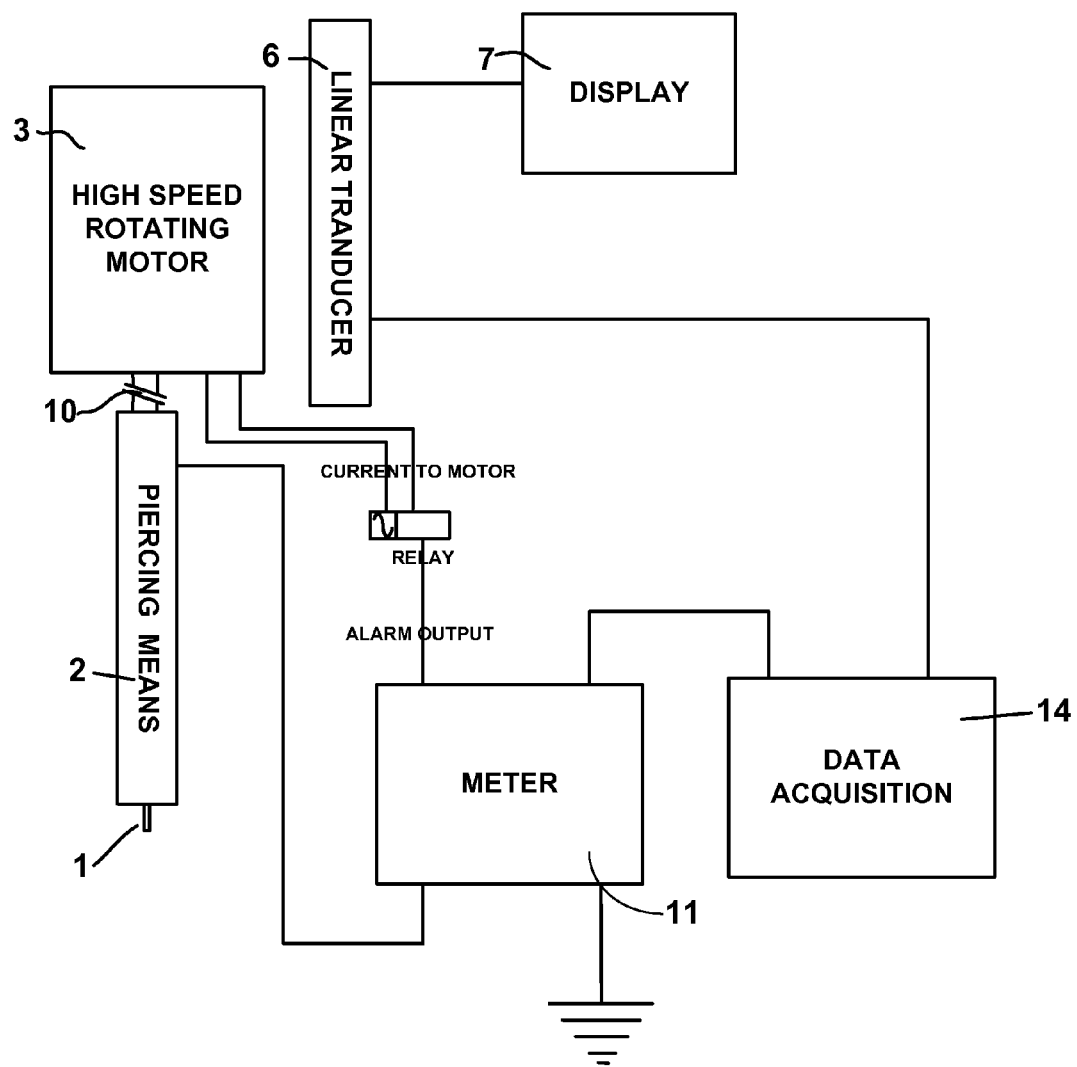
FIG. 1 is a block flow diagram of the complete system including the delivery assembly, meter and data acquisition device.

The preferred embodiment consists of a test piercing assembly that is made up of a slender piercing tool rod or filament 1. It is understood that the piercing tool rod may be any material that is of sufficiently high melting temperature relative to the substance to be pierced, so-as to sustain the friction-flow piercing process as described above. The filament is comprised of tungsten in the preferred embodiment, but other metals or composites are anticipated.

A slender filament of sufficient length will require external support to prevent buckling under the piercing pressure. If a support is required, it is understood that support means may be a meltable, tubular support 2 casement comprised of styrene or another suitable low temperature meltable material. Alternatively a mechanical system providing a plurality of support locations along the axis of the piercing means including, but not limited to, collapsible leaf type springs or a lever system typical of an industrial scissor-lift apparatus or a coil spring may be used. A more elaborate powered system could retract the supports in a controlled manner adding the advantage of a controlled piercing rate.

The delivery method may include a high speed rotational motor such as a "Dremel" type motor 3 having a slidably mounted depth guide 4 with a slip-axis parallel to the major axis of the piercing tool, and surfaces 5 that contact the work surface near where the piercing tool enters the work. A linear transducer 6 capable of zeroing at any location and having a read-out 7 to provide linear displacement information, and alternatively, the capability to output that data to a data acquisition device for processing is connected between the motor 3 and the depth guide 4 to monitor piercing depth. A non-contact micrometer such as ultrasonic is anticipated. A depth limiting stop 8 may be provided so that the maximum piercing depth can be pre-set. A chuck 9 is fitted to the motor to accept the piercing tool 1 and, if required, the meltable tubular support 2. An insulation barrier 10 is positioned to prevent current from the electrical meter 11, contacting the motor or the linear transducer 6 components. A lead from an electrical instrument such as a meg-ohm insulation meter 11 is slipably attached 12 to the chuck 9 so that the meter is in constant electrical contact with the piercing tool during the piercing process, but is insulated from the rest of the apparatus.

The meter 11 may be comprised of an alarm 13 that registers sudden-changes in conductivity and will cause the motor 3 to quit and prevent further piercing. Alternately, the meter may also be capable of outputting its data to an external acquisition device 14.

An optional data acquisition device 14 may be used to collect data from the linear transducer 6 and compare it graphically, in real time with data from the meter 11, and produce a thickness versus resistivity/capacitance profile of the laminate. It is anticipated that the data acquisition unit 14 and the meter 11 may be a single, combined device.

It is anticipated that the permanently installed filaments may be hard-wired-electrically connected to a system that monitors the electrical condition of the substrate on an intermittent or continuous basis and warns the owner of the equipment of a change in electrical properties thereby eliminating the need for monitoring by hand.

DESCRIPTION OF THE DRAWINGS

FIG. 1: Block flow diagram of complete system including the delivery assembly, meter 11, and data acquisition device 14.

Figure 2:
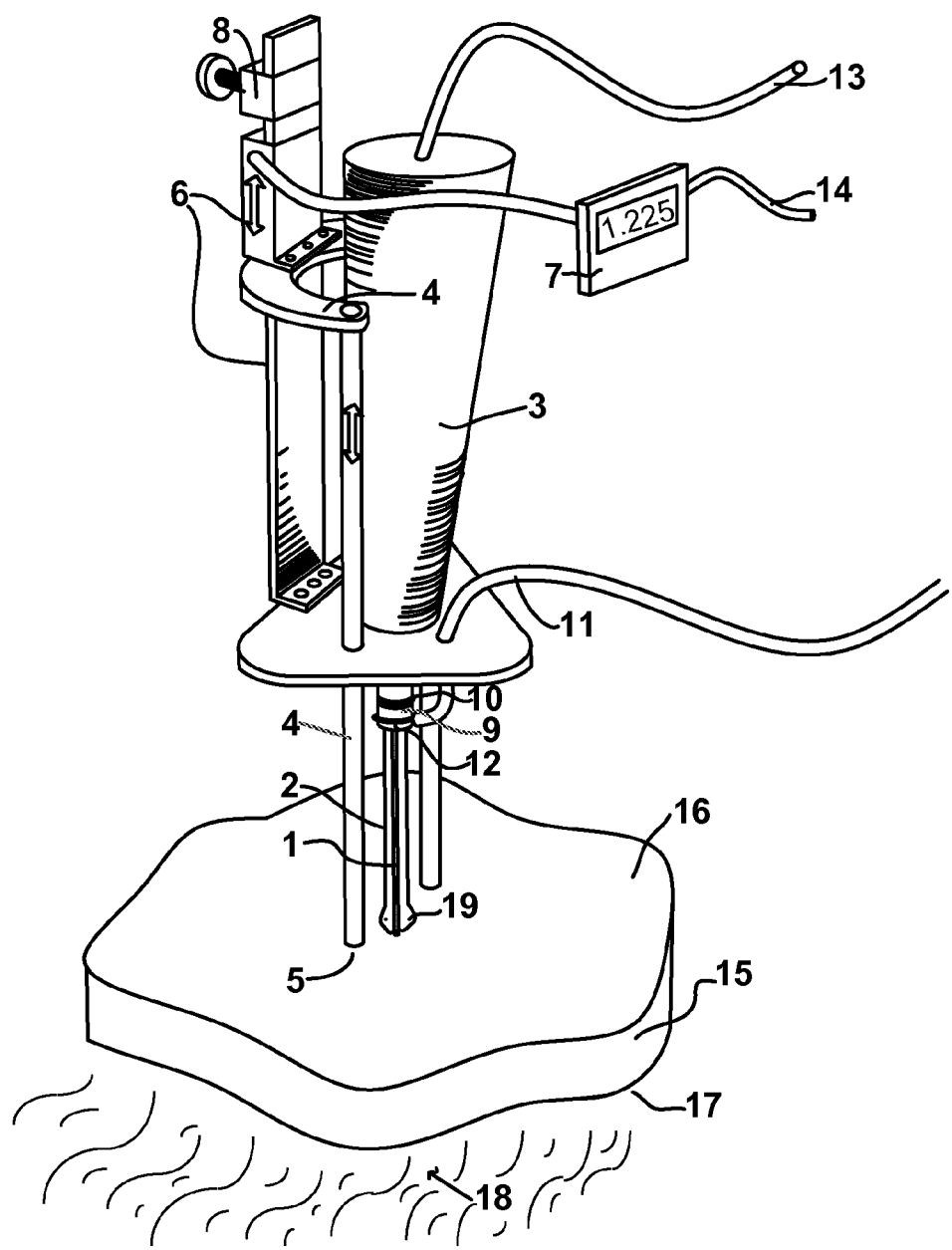
FIG. 2 is the filament delivery assembly including the drive motor, chuck, sliding depth guide, linear transducer and depth stop with piercing assembly inserted.

FIG. 2: The filament delivery assembly including the drive motor 13, chuck 9, sliding depth guide 4, linear transducer 6, depth stop 8 with piercing assembly inserted 1, 2.

Figure 3:
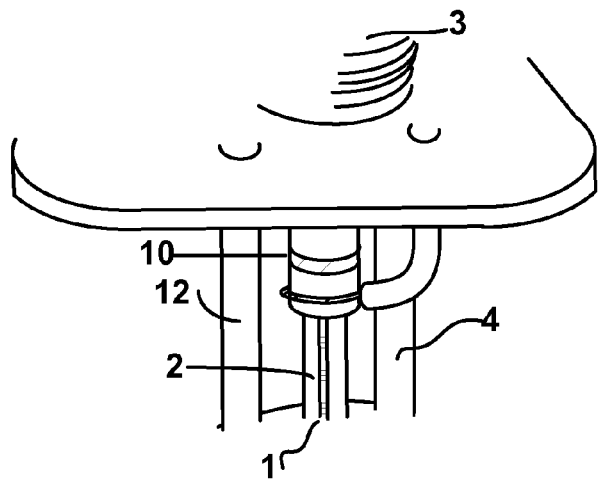
FIG. 3 is a close up of the chuck.

FIG. 3: Close up of the chuck 9.

Figure 4:
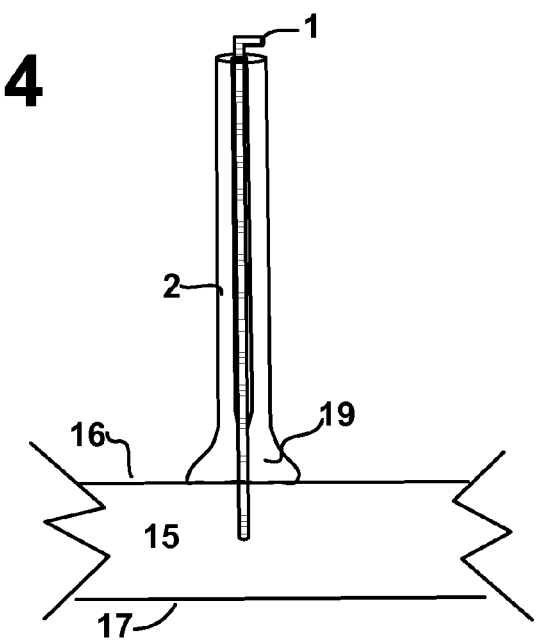
FIG. 4 is a close up of the piercing means inserted into the work including the piercing rod and the meltable sheath.

FIG. 4: Close up of piercing means inserted into the work including the piercing rod and the meltable sheath. 1, 2.

Figure 5:
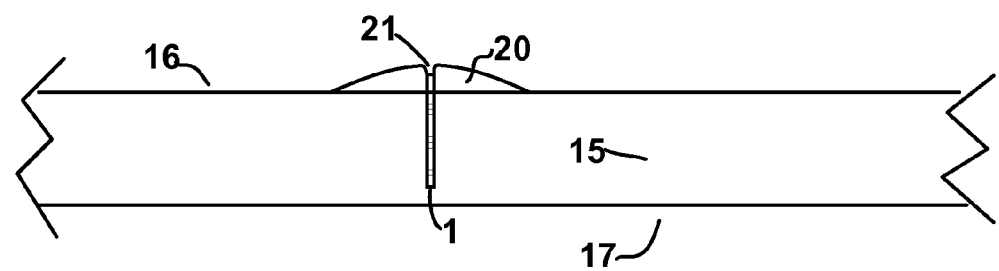
FIG. 5 is the installed filament sealed in place with the exposed electrical terminal.

FIG. 5: Installed filament sealed in place 20 with exposed electrical terminal 21.

What is claimed is:

1. An apparatus for the permanent insertion of a slender, high aspect ratio non-consumable conductive filament into a substantially planar dielectric substrate having a working surface and an opposing surface, via the process of rotational friction piercing for the purpose of measuring the substrates electrical properties without substantially disturbing the substrates structural integrity comprising:
   a filament, one end fitted to a rotational means, an opposite end of the filament positioned adjacent to the working surface of the substrate with the axis of the filament substantially normal to a major plane of the dielectric substrate,
   and device will be comprised of a means to advance the opposing end of the filament into the surface of the substrate, the leading opposite end of the filament will be maintained in a lateral position, relative to the plane of the substrate to prevent lateral movement along the plane during insertion,
   the filament is electrically connected to a lead of an electrical meter during or after insertion, which is electrically connected to conductive surfaces in contact with the opposite side of the dielectric substrate, a measuring current between the filament and said opposing side of substrate be insufficient to impart substantial additional heat to the substrate or the filament during the measuring process.

2. An apparatus as in claim 1 wherein the rotational means is comprised of a rotational motor.

3. An apparatus as in claim 1 wherein the means to advance is comprised of a slidably attached guide member, an end of which may contact the working surface, which is adapted to slide along said axis of the filament.

4. The apparatus as in claim 3 having a linear transducer that is affixed between the filament and the sliding guide member so that the distance traveled by the filament relative to said guide member is measured.

5. An apparatus as in claim 4 wherein the sliding guide member or said linear transducer are comprised of a positive stop to establish a maximum piercing depth.

6. An apparatus as in claim 3 wherein the guide member is mechanically retracted by powered actuators to advance the rotating filament into the material of the dielectric substrate.

7. An apparatus as in claim 1 wherein the meter is comprised of an alarm that warns of changes in dielectric properties within the substrate.

8. An apparatus as in claim 7 wherein the rotational drive motor is shut down in response to the alarm.

9. An apparatus as in claim 1 further comprised of a data acquisition module that collects output of the meter and the linear transducer.

10. An apparatus as in claim 9 wherein said output from the meter and the linear transducer are correlated with each other in time.

11. An apparatus as in claim 1 wherein the filament is covered with a coating, except for the piercing end, said coating electrically insulates the shank of the filament from the material of the solid body except at the piercing end.

12. The apparatus as in 11 wherein the coating is comprised of non-conductive ceramic or glass.

13. An apparatus as in claim 1 wherein the filament is not withdrawn from the material of the solid body and the mounting end of the filament remains exposed for electrical contact on the working surface.

14. An apparatus as in claim 3 further comprised of a consumable tubular filament buckling support means having a central axis, the conductive filament having a major axis that is positioned substantially along the central axis of the tubular support means such that the filament is positioned within the tubular support and the material of the tubular buckling support means is consumed by melting as the filament is inserted into the dielectric substrate.

15. The apparatus as in claim 13 wherein the inserted filament is electrically connected to a monitoring system such that the electrical properties of the dielectric solid is measured periodically or continuously.

16. A method for determining the electrical properties of a dielectric solid, said solid having a working surface and an opposing surface in electrical contact with a conductive media, the method comprising:
   a step of providing an elongated electrically conductive rod that is held substantially normal to said working surface;
   advancing said conductive rod into the dielectric substrate by a process of rotational friction piercing,
   attaching one lead of an electrical meter having at least two leads which will be held in electrical contact with a surface of the rod during or after insertion, another lead of the meter will be held in electrical contact with the conductive media;
   measuring the electrical properties of the solid with the electrical meter.

17. The method as in claim 16 further incorporating a step of leaving the rod embedded in the dielectric substrate after insertion such that the working surface of the rod is available for intermittent or continuous electrical contact with a meter to monitor so the electrical properties of the substrate.

18. The method as in claim 16 further incorporating the step of coating the rod with a nonconductive coating on the exterior except at the piercing end and the contact with a lead of the meter so that the electrical condition of the substrate is measured only from the tip of the rod.

19. The method as in claim 16 wherein the advancement of the rod is measured and the results recorded by a data acquisition device.

20. The method as in claim 19 wherein the movement of the rod and the output no from the meter are collected by the data acquisition device.

* * * * *